United States Patent [19]

Butti et al.

[11] 4,093,730

[45] June 6, 1978

[54] METHODS OF USING SPERMICIDAL VAGINAL COMPOSITIONS COMPRISING 1,2-BENZISOTHIAZOLE DERIVATIVES

[75] Inventors: Adriano Butti, Como; Giovanni Gazzani, Appiano Gentile, both of Italy

[73] Assignee: Prephar Prospection de Recherches Pharmaceutiques S.A., Vordergasse, Switzerland

[21] Appl. No.: 700,115

[22] Filed: Jun. 28, 1976

[30] Foreign Application Priority Data

Jul. 3, 1975 Italy .................................. 25051 A/75

[51] Int. Cl.² ................................................ A61K 31/425
[52] U.S. Cl. ........................... 424/270; 424/DIG. 14
[58] Field of Search ......................... 424/270, DIG. 14

[56] References Cited

U.S. PATENT DOCUMENTS 3,012,039  12/1961  Morley ............................. 424/270 X

OTHER PUBLICATIONS

Chemical Abstracts 69:10423d (1968).

*Primary Examiner*—Leonard Schenkman
*Attorney, Agent, or Firm*—Browdy and Neimark

[57] ABSTRACT

A spermicidal vaginal composition comprises a spermicidal-effective amount of a 1,2-benzisothiazole derivative having the general formula (I)

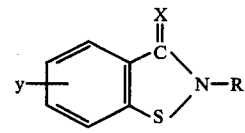

wherein:
  X is either O or S;
  y is H; $NO_2$; an halogen atom or an alkyl radical having from 1 to 4 carbon atoms; and
  R is H; a straight or branched alkyl or alkenyl radical having from 1 to 6 carbon atoms, optionally substituted by one or more hydroxyl, tertiary amino and alkoxyl groups; a cycloaliphatic radical having from 3 to 8 carbon atoms; an aryl radical optionally substituted by halogen atoms, alkyl or alkoxy radicals; an aralkyl radical optionally having the aromatic moiety substituted by halogen atoms, alkyl and alkoxyl radicals; or an acyl radical —COR' wherein R' is an alkyl group having from 1 to 4 carbon atoms or an aryl radical.

15 Claims, No Drawings

METHODS OF USING SPERMICIDAL VAGINAL COMPOSITIONS COMPRISING 1,2-BENZISOTHIAZOLE DERIVATIVES

BACKGROUND OF THE INVENTION

1. Field of the Invention

The present invention relates to spermicidal compositions. More particularly the present invention relates to spermicidal vaginal compositions comprising as active agent a compound belonging to a class of known 1,2-benzisothiazole derivatives, the powerful spermicidal activity of which, however, had never been previously noticed.

2. Description of the Prior Art

Contraceptive agents have long been known, which upon introduction into the vaginal canal in the form of suitable compositions, such as suppositories, tablets, vaginal creams and the like, kill human spermatic cells or at least inhibit their ability to effect conception.

Among the most active known spermicidal agents are the alkylphenoxy polyethoxyethanols (e.g. "Nonoxynol"), certain quaternary ammonium compounds (e.g. benzethonium chloride) and organo-mercurial compounds (e.g. phenylmercury nitrate).

While on one hand such known spermicidal agents are generally satisfactory, it is on the other hand apparent that it is desirable to find other substances which, apart from exhibiting all of the other advantageous characteristics of the known spermicidal agents, such as for instance a substantial absence of any undesired side-effect, are endowed with a more powerful spermicidal action.

1,2-benzisothiazole and its derivatives 1,2-benzisothiazolone and 1,2-benzisothiazole-3-thione have long since been known.

Specifically, there are known 1,2-benzisothiazole derivatives falling within the general formula (I)

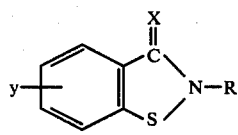

wherein:

$X$ is either O or S;

$y$ is H; $NO_2$; an halogen atom or an alkyl radical having from 1 to 4 carbon atoms; and R is H; a straight or branched alkyl or alkenyl radical having from 1 to 6 carbon atoms, optionally substituted having from 1 to 6 carbon atoms, optionally substituted by one or more hydroxyl, tertiary amino and alkoxyl groups; a cycloaliphatic radical having from 3 to 8 carbon atoms; an aryl radical optionally substituted by halogen atoms, alkyl or alkoxyl radicals; an aralkyl radical optionally having the aromatic moiety substituted by halogen atoms, alkyl and alkoxyl radicals; or an acyl radical —COR' wherein R' is an alkyl group having from 1 to 4 carbon atoms or an aryl radical.

For a general treatment of these compounds reference is made e.g. to "Advances in heterocyclic chemistry" Vol. 14, pages 43-93 (1972) Academic Press, Inc.

Of these compounds, only their antibacterial and fungicidal activity was previously known. So, for instance, U.S. Pat. No. 3,012,039 discloses that certain 1,2-benzisothiazolone derivatives having the general formula:

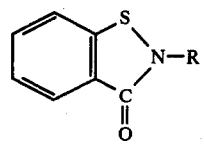

wherein R is an alkyl radical, a benzyl radical substituted by halogens; a phenyl radical substituted by an alkyl radical, etc., possess useful antibacterial and antifungal activity.

U.S. Pat. No. 3,065,123 discloses that certain 1,2-benzisothiazolone derivatives having the general formula:

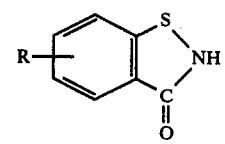

wherein R is selected from the group consisting of hydrogen and halogen atom(s), possess antimicrobical activity.

Also British Pat. No. 967,028 and U.S. Pat. Nos. 3,517,022; 3,761,489; 3,821,389 and 3,862,955 disclose the synthesis and the fungicidal and bactericidal activity of certain benzisothiazole derivatives falling within general formula (I).

The local anesthetic activity of certain 3-alkylaminoalkoxy-1,2-benzisothiazoles has been disclosed by T. Vitali et al in "I/ farmaco" Vol. 23, No. 11, pages 1081-9.

R. Fisher et al have disclosed in Arzneimittel-Forsch 14(12), 1301-6 (1964) that certain benzisothiazolones, among which is N-n-butyl-benzisothiazolone, have a wide range of bacteriostatic and fungistatic activity.

All the patents and articles previously mentioned are herein incorporated by reference.

SUMMARY OF THE INVENTION

It has now surprisingly been found that the compound belonging to formula (I) some of which are per se known 1,2-benzisothiazole derivatives, present extraordinary spermostatic and spermicidal activities previously never noticed, which exceed even by hundreds of times the activities of the above mentioned known spermicides.

According to the present invention, there is provided a spermicidal vaginal composition comprising an inert vaginal excipient and a spermicidal-effective amount of a 1,2-benzisothiazole derivative having the general formula (I)

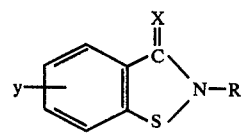

wherein:

X is either O or S;

$y$ is H; $NO_2$; an halogen atom or an alkyl radical having from 1 to 4 carbon atoms; and R is H; a straight or branched alkyl or alkenyl radical having from 1 to 6 carbon atoms, optionally substituted by one or more hydroxyl, tertiary amino and alkoxyl groups; a cycloaliphatic radical having from 3 to 8 carbon atoms; an aryl radical optionally substituted by halogen atoms, alkyl or alkoxy radicals; an aralkyl radical optionally having the aromatic moiety substituted by halogen atoms, alkyl and alkoxyl radicals; or an acyl radical —COR' wherein R' is an alkyl group having from 1 to 4 carbon atoms or an aryl radical.

DESCRIPTION OF THE PREFERRED EMBODIMENT

In the compositions according to the invention, the amount of the 1,2-benzisothiazole derivative of general formula (I) is preferably between 0.1 and 1% by weight based on the composition.

Among the benzisothiazole derivatives of general formula (I), the following are particularly preferred insofar as they are the most active:
N-n-butyl 1,2-benzisothiazolone
N-acetyl 1,2-benzisothiazolone
N-2-hydroxyethyl 1,2-benzisothiazole-3-thione
N-diethylaminoethyl-1,2-benzisothiazolone hydrochloride
N-n-propyl 1,2-benzisothiazole-3-thione
N-iso-propyl 1,2-benzisothiazole-3-thione
6-nitro N-acetyl 1,2-benzisothiazolone
5-nitro N-n-butyl 1,2-benzisothiazolone
5-nitro N-methyl 1,2-benzisothiazolone
N-ethyl 1,2-benzisothiazole-3-thione The effectiveness of the 1,2-benzisothiazole derivatives belonging to the class having general formula (I) has been checked both from the standpoint of their spermostatic activity and spermicidal activity, by using the following procedures:

(A) Inhibiting activity on the spermatic cell motility (spermostatic activity).

All of the solutions in saline (0.9% by weight solution of sodium chloride in distilled water) of the substances under examination were brought, before testing them, to pH value of 7.3 with diluted NaOH or HCl, in order to avoid any possibility that the hydrogen ion concentration might affect the spermatic cell motility.

The substances which were insoluble in saline were subjected to thorough grinding in a suitable colloid mill to obtain a homogeneous dispersion. One drop of human sperm and one drop of the substance to be tested dissolved in saline were placed on a slide.

The two drops were immediately thoroughly mixed with a thin glass rod, with maintenance of mixing for about 10 seconds.

On the dispersion thus obtained, a slide was placed and the spermatic cell motility was immediately observed (five fields of view at various magnifications).

The controls were repeated after 15, 30, 60 and 90 minutes, respectively.

For each group of tests, a control test using saline only (volume ratio sperm/saline 1:1) was carried out, in order to verify whether the spermatic cell movements were normal.

The results based on the motility degree shown by the spermatic cells, are expressed by the following symbols:
— complete stopping of any movement
+ — just perceptible signs of motility
+ fair motility
+ + normal motility In the following examples there is shown the spermostatic activity of some 1,2-benzisothiazole derivatives belonging to the class of general formula (I), as a function of the concentration. The tests were carried out by following the procedures previously outlined. For each Example the control test showed that the spermatic cells possessed normal motility.

EXAMPLE I

5-chloro 1,2-benzisothiazolone

| Concentration | MOTILITY (in minutes) | | | | |
|---|---|---|---|---|---|
| | Immediately | After 15 | 30 | 60 | 90 |
| 0.1% | — | — | — | — | — |
| 0.01% | — | — | — | — | — |
| 0.05% | — | — | — | — | — |
| 0.0025% | — | — | — | — | — |
| 0.00125% | + — | — | — | — | — |
| 0.000625% | + | + — | — | — | — |
| 0.000312% | + | + | + — | — | — |

EXAMPLE 2

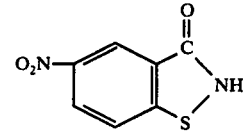

5-nitro 1,2-benzisothiazolone

| Concentration | MOTILITY (in minutes) | | | | |
|---|---|---|---|---|---|
| | Immediately | After 15 | 30 | 60 | 90 |
| 0.1% | — | — | — | — | — |
| 0.01% | + — | — | — | — | — |
| 0.005% | + — | — | — | — | — |
| 0.0025% | + | — | — | — | — |

EXAMPLE 3

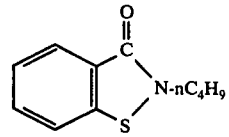

N-n butyl 1,2-benzisothiazolone

| Concentration | MOTILITY (in minutes) | | | | |
|---|---|---|---|---|---|
| | Immediately | After 15 | 30 | 60 | 90 |
| 0.1% | — | — | — | — | — |
| 0.01% | — | — | — | — | — |
| 0.005% | — | — | — | — | — |
| 0.0025% | — | — | — | — | — |
| 0.00125% | — | — | — | — | — |
| 0.000625% | + — | — | — | — | — |
| 0.0003125% | + + | — | — | — | — |
| 0.0001562% | + + | + | — | — | — |

EXAMPLE 4

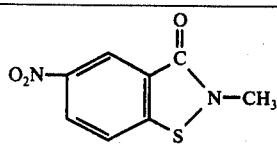

MOTILITY (in minutes)

| Concentration | Immediately | After 15 | 30 | 60 | 90 |
|---|---|---|---|---|---|
| 0.1% | − | − | − | − | − |
| 0.01% | − | − | − | − | − |
| 0.005% | − | − | − | − | − |
| 0.0025% | − | − | − | − | − |
| 0.00125% | − | − | − | − | − |
| 0.000625% | − | − | − | − | − |
| 0.000312% | − | − | − | − | − |
| 0.000156% | + | + | + | + | + |

EXAMPLE 5

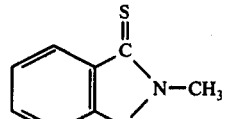

5-nitro N-n butyl 1,2-benzisothiazolone

MOTILITY (in minutes)

| Concentration | Immediately | After 15 | 30 | 60 | 90 |
|---|---|---|---|---|---|
| 0.1% | − | − | − | − | − |
| 0.01% | − | − | − | − | − |
| 0.005% | − | − | − | − | − |
| 0.0025% | − | − | − | − | − |
| 0.00125% | − | − | − | − | − |
| 0.000625% | + | +− | − | − | − |

EXAMPLE 6

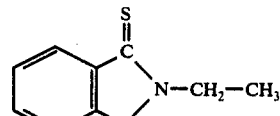

6-nitro N-n butyl 1,2-benzisothiazolone

MOTILITY (in minutes)

| Concentration | Immediately | After 15 | 30 | 60 | 90 |
|---|---|---|---|---|---|
| 0.1% | − | − | − | − | − |
| 0.01% | − | − | − | − | − |
| 0.005% | − | − | − | − | − |
| 0.0025% | +− | − | − | − | − |
| 0.00125% | ++ | + | + | − | − |

EXAMPLE 7

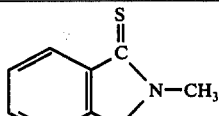

N-methyl 1,2-benzisothiazole-3-thione

MOTILITY (in minutes)

| Concentration | Immediately | After 15 | 30 | 60 | 90 |
|---|---|---|---|---|---|
| 0.1% | − | − | − | − | − |
| 0.01% | − | − | − | − | − |
| 0.005% | − | − | − | − | − |
| 0.0025% | − | − | − | − | − |
| 0.00125% | +− | − | − | − | − |
| 0.000625% | +− | − | − | − | − |
| 0.000312% | ++ | − | − | − | − |

-continued

N-methyl 1,2-benzisothiazole-3-thione

MOTILITY (in minutes)

| Concentration | Immediately | After 15 | 30 | 60 | 90 |
|---|---|---|---|---|---|
| 0.000156% | ++ | ++ | + | +− | − |

EXAMPLE 8

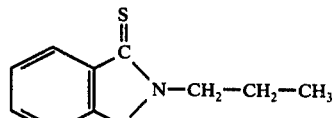

N-ethyl 1,2-benzisothiazole-3-thione

MOTILITY (in minutes)

| Concentration | Immediately | After 15 | 30 | 60 | 90 |
|---|---|---|---|---|---|
| 0.05% | − | − | − | − | − |
| 0.01% | − | − | − | − | − |
| 0.005% | − | − | − | − | − |
| 0.0025% | − | − | − | − | − |
| 0.00125% | − | − | − | − | − |
| 0.000625% | +− | − | − | − | − |
| 0.000312% | + | − | − | − | − |

EXAMPLE 9

N-n-propyl 1,2-benzisothiazole-3-thione

MOTILITY (in minutes)

| Concentration | Immediately | After 15 | 30 | 60 | 90 |
|---|---|---|---|---|---|
| 0.01% | − | − | − | − | − |
| 0.005% | − | − | − | − | − |
| 0.0025% | − | − | − | − | − |
| 0.00125% | − | − | − | − | − |
| 0.000625% | + | +− | − | − | − |

EXAMPLE 10

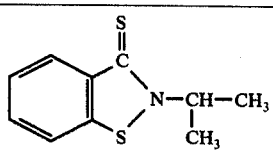

N-isopropyl 1,2-benzisothiazole-3-thione

MOTILITY (in minutes)

| Concentration | Immediately | After 15 | 30 | 60 | 90 |
|---|---|---|---|---|---|
| 0.01% | − | − | − | − | − |
| 0.005% | − | − | − | − | − |
| 0.0025% | − | − | − | − | − |
| 0.00125% | − | − | − | − | − |
| 0.000625% | + | +− | − | − | − |

EXAMPLE 11

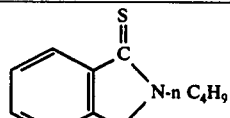

N-n butyl 1,2-benzisothiazole-3-thione

| Concentration | MOTILITY (in minutes) | | | | |
|---|---|---|---|---|---|
| | Immediately | After 15 | 30 | 60 | 90 |
| 0.1% | − | − | − | − | − |
| 0.05% | − | − | − | − | − |
| 0.35% | − | − | − | − | − |
| 0.025% | +− | − | − | − | − |
| 0.015% | + | − | − | − | − |
| 0.010% | + | +− | − | − | − |

EXAMPLE 12

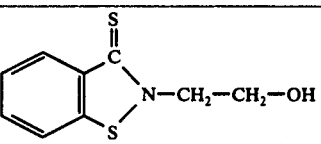

N-2-hydroxyethyl 1,2-benzisothiazole-3-thione

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | − | − | − | − | − |
| 0.00125% | − | − | − | − | − |
| 0.000625% | +− | − | − | − | − |
| 0.0003125% | ++ | − | − | − | − |
| 0.0001562% | ++ | + | +− | − | − |

EXAMPLE 13

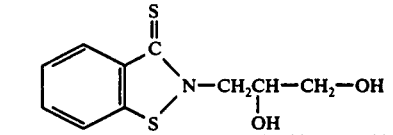

N-2,3-dihydroxypropyl 1,2-benzisothiazole-3-thione

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | +− | − | − | − | − |
| 0.000125% | ++ | + | +− | − | − |

EXAMPLE 14

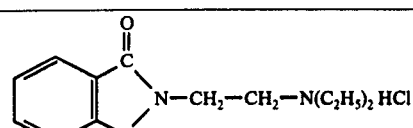

N-diethylaminoethyl 1,2-benzisothiazole-3-thione hydrochloride

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.05% | − | − | − | − | − |
| 0.0025% | − | − | − | − | − |
| 0.00125% | − | − | − | − | − |
| 0.00625% | − | − | − | − | − |
| 0.0003125% | +− | − | − | − | − |
| 0.0001562% | ++ | +− | − | − | − |

-continued

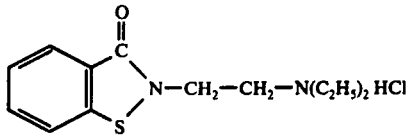

N-diethylaminoethyl 1,2-benzisothiazole-3-thione hydrochloride

| Concentration | MOTILITY (in minutes) | | | | |
|---|---|---|---|---|---|
| | Immediately | After 15 | 30 | 60 | 90 |
| 0.0000781% | ++ | ++ | ++ | + | + |

EXAMPLE 15

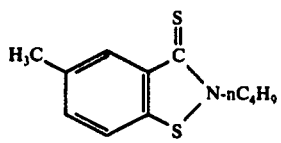

5-methyl N-n butyl 1,2-benzisothiazole-3-thione

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.001% | ++ | + | + | − | − |

EXAMPLE 16

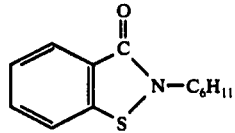

N-cyclohexyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.001% | ++ | ++ | ++ | + | + |

EXAMPLE 17

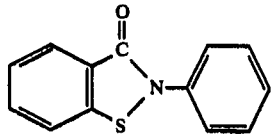

N-phenyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | +− | − | − | − | − |
| 0.005% | + | − | − | − | − |
| 0.0025% | ++ | ++ | + | + | + |

EXAMPLE 18

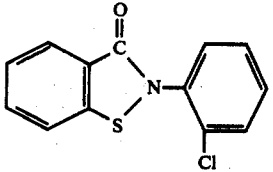

N-o-chlorophenyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | +− | − | − | − | − |
| 0.00125% | + | + | − | − | − |
| 0.000625% | + | + | + | +− | − |

EXAMPLE 19

N-n-chlorophenyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | +− | − | − | − | − |
| 0.00125% | + | + | +− | − | − |

EXAMPLE 20

N-p-methoxyphenyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | +− | − | − | − | − |
| 0.05% | + | +− | − | − | − |
| 0.0025% | ++ | + | + | − | − |

EXAMPLE 21

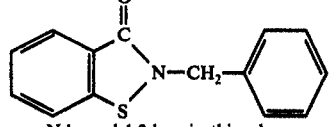

N-benzyl 1,2-benzisothiazolone

| Concentration | MOTILITY (in minutes) | | | | |
|---|---|---|---|---|---|
| | Immediately | After 15 | 30 | 60 | 90 |
| 0.01% | − | − | − | − | − |
| 0.005% | − | − | − | − | − |
| 0.0025% | − | − | − | − | − |
| 0.00125% | + | − | − | − | − |

EXAMPLE 22

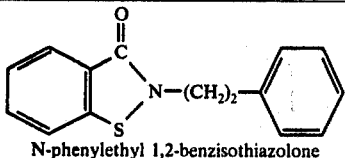

N-phenylethyl 1,2-benzisothiazolone

| Concentration | MOTILITY (in minutes) | | | | |
|---|---|---|---|---|---|
| | Immediately | After 15 | 30 | 60 | 90 |
| 0.001% | − | − | − | − | − |
| 0.005% | − | − | − | − | − |
| 0.0025% | − | − | − | − | − |
| 0.00125% | + | − | − | − | − |

EXAMPLE 23

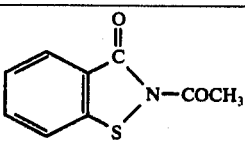

N-acetyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | − | − | − | − | − |
| 0.00125% | − | − | − | − | − |
| 0.000625% | +− | − | − | − | − |
| 0.0003125% | ++ | − | − | − | − |
| 0.0001562% | ++ | + | +− | − | − |

EXAMPLE 24

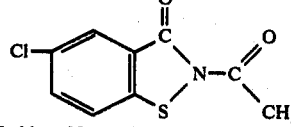

5-chloro N-acetyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | +− | − | − | − | − |
| 0.0025% | + | − | − | − | − |
| 0.00125% | + | +− | − | − | − |

EXAMPLE 25

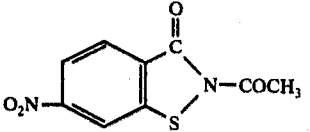

6-nitro N-acetyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | − | − | − | − | − |
| 0.00125% | − | − | − | − | − |
| 0.000625% | +− | − | − | − | − |
| 0.000312% | ++ | ++ | + | + | + |

EXAMPLE 26

6-nitro N-propionyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | +− | − | − | − | − |
| 0.0025% | ++ | + | − | − | − |

EXAMPLE 27

5-nitro N-benzoyl 1,2-benzisothiazolone

| Concentration | MOTILITY (in minutes) | | | | |
|---|---|---|---|---|---|
| | Immediately | After 15 | 30 | 60 | 90 |
| 0.1% | − | − | − | − | − |
| 0.01% | − | − | − | − | − |
| 0.005% | − | − | − | − | − |
| 0.0025% | +− | +− | − | − | − |

EXAMPLE 28

6-nitro N-benzoyl 1,2-benzisothiazolone

| Concentration | MOTILITY (in minutes) | | | | |
|---|---|---|---|---|---|
| | Immediately | after 15 | 30 | 60 | 90 |
| 0.1% | − | − | − | − | − |
| 0.01% | − | − | − | − | − |
| 0.005% | +− | − | − | − | − |
| 0.0025% | ++ | − | − | − | − |
| 0.00125% | ++ | + | +− | − | − |

(B) Spermicidal activity

The following solutions were prepared:
(a) Nutrient solution at pH 7.4 having the following composition:

| NaCl | sol. | 0.154 M | 100.0 | c.c. |
|---|---|---|---|---|
| KCl | " | 0.154 M | 2.0 | " |
| CaCl$_2$ (anhydrous) | " | 0.110 M | 2.0 | " |
| NaHCO$_3$ | " | 0.154 M | 20.0 | " |
| (*) phosphate-containing buffer | " | 0.109 M (*) | 10.0 | " |
| Fructose | 10% | | 2.7 | " |

(*) Phosphate-containing buffer composition:

| Na$_2$HPO$_4$ | 1.268 g. |
|---|---|
| NaH$_2$PO$_4$ | 0.248 g. |
| H$_2$O (distilled) | 100.0 c.c. |

(b) Spermatic cell suspension diluted 1:10 with nutrient solution (a)

(c) 0.0014% solution of the 1,2-benzisothiazole derivative of formula (I) in nutrient solution (a). Specifically, the compounds of Examples 3, 12, 14 and 23 were tested.

In a test tube there were placed 1 ml of the spermatic cell suspension (b) and 9 ml of the nutrient solution (a). After careful mixing, 5 ml of the suspension thus obtained were drawn and added to 5 ml of solution (c). After mixing, the stop watch was started.

At time intervals of 1, 5, 10 and 20 minutes, 1 ml of the suspension was drawn and immediately diluted in a test tube with 9 ml of nutrient solution (a).

The test tubes were subjected to centrifugation at 4000 revolutions for 5 minutes. Subsequently, the supernatant phase was discarded and the spermatic cells were taken up with 10 ml of nutrient solution (a) alone. After a further centrifugation, the spermatic cells were again taken up with 4 ml of the same nutrient solution (a).

One then observed microscopically whether the movements of the spermatic cells were present. The microscopical observations were repeated after 5, 10, 30, 60 and 120 minutes, by keeping the suspensions of the spermatic cells at 37° C.

As result, it was observed that in no case was there a resumption of the spermatic cell motility.

Therefore, the previous 1,2-benzisothiazole derivatives present, under the experimental conditions above indicated, a lethal action towards the spermatic cells. Consequently, such derivatives are not only endowed with spermostatic activity but also with spermicidal action.

As previously mentioned, the 1,2-benzisothiazole derivatives of general formula (I) have activity remarkably superior to that of the known spermicidal agents. For instance, the compounds of Examples 3, 12 and 23 have activity one hundred times higher than that of Nonoxynol, thirty-three times higher than that of benzethonium chloride and four times higher than that of phenyl-mercury nitrate, while the compound of Example 14 is two hundred times more active than Nonoxynol, sixty-six times more active than benzethonium chloride and eight times more active than phenyl-mercury nitrate.

In order to prepare the compositions of the present invention, the 1,2-benzisothiazole derivatives of general formula (I) are compounded according to the procedures which are conventional in this field, by employing the usual additives, excipients, emulsifying agents and the like, the choice and amount of which will be apparent to those skilled in this art.

Some examples are herebelow given relating to spermicidal compositions according to the invention, which contain the compounds of Examples 3, 12, 14 and 23.

Vaginal suppositories

Composition for a 3-gram suppository:

| Compound of Example 3 or 12 or 14 or 23 | 0.005 g |
|---|---|
| Hexantriol | 0.1 g |
| Polyglycol 1500 | balance to 3 g |

Vaginal tablets

Composition for a 2-gram tablet:

| Compound of Example 3 or 12 or 14 or 23 | 0.004 g |
|---|---|
| Anhydrous citric acid | 0.7 g |
| Sodium bicarbonate | 0.3 g |
| Polyglycol 6000 | 0.4 g |
| Lactose | balance to 2 g |

| Vaginal cream | | |
|---|---|---|
| Percentage composition: | | |
| Compound of Example 3 or 12 or 14 or 23 | 1 | g |
| Nonionic autoemulsifying base | 4 | g |
| Water balance to | 100 | g | for each application, 0.5 grams of the cream are vaginally administered with a suitable syringe.

| Water-soluble vaginal cream | | |
|---|---|---|
| Percentage compositions: | | |
| Compound of Example 3 or 12 or 14 or 23 | 1 | g |
| Polyglycol 400 | 30 | g |
| Polyglycol 400 | 30 | g |
| Polyglycol 6000 | 8.5 | g |
| Hexantriol | 3 | g |
| Water balance to | 100 | g |

For each application, 0.6 grams of the cream are vaginally administered with a suitable syringe.

| Vaginal spray-foam | | |
|---|---|---|
| Percentage composition: | | |
| Compound of Example 3 or 12 or 14 or 23 | 1 | g |
| Polyglycol 6000 | 2 | g |
| Nonionic emulsifying agent | 2 | g |
| Water | 85 | g |
| Freon 12/114 (70.30) | 10 | g |

For each application, 0.5 grams of the foam are vaginally administered.

| Vaginal soluble waffle | |
|---|---|
| Composition for one 0.340-gram waffle: | |
| Compound of Example 3 or 12 or 14 or 23 | 0.003 g |
| Starch | 0.040 g |
| Water-soluble lanolin | 0.340 g |

The preferred range of dosage is from about 0.003 grams to 0.010 grams of active substance, i.e. of 1,2-benzisothiazole derivative, for each vaginal administration.

What is claimed is:

1. A method of contraception, comprising; administering to a disease free human vagina immediately prior to coitus a spermatocidally effective amount of a 1,2-benzisothiazole derivative having the general formula

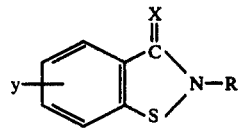

wherein:

X is either O or S;

$y$ is H, $NO_2$, a halogen atom or an alkyl radical having 1–4 carbon atoms; and R is H; a straight or branched alkyl or alkenyl radical having from 1–6 carbon atoms, optionally substituted by one or more hydroxyl or tertiary amino groups; a cycloaliphatic radical having from 3 to 8 carbon atoms; a phenyl radical, optionally substituted by halogen atoms or methoxy radicals; a benzyl or phenylethyl radical; or an acyl radical, —$COR^1$, wherein $R^1$ is an alkyl group having from 1 to 4 carbon atoms or a phenyl radical.

2. The method of claim 1, wherein said 1,2-benzisothiazole derivative is N-n-butyl 1,2-benzisothiazolone.

3. The method of claim 1, wherein said 1,2-benzisothiazole derivative is N-acetyl 1,2-benzisothiazole-3-thione.

4. The method of claim 1, wherein said 1,2-benzisothiazole derivative is N-2-hydroxyethyl 1,2-benzisothiazole-3-thione.

5. The method of claim 1, wherein said 1,2-benzisothiazole derivative is N-diethylaminoethyl 1,2-benzisothiazolone hydrochloride.

6. The method of claim 1, wherein said 1,2-benzisothiazole derivative is N-n-propyl 1,2-benzisothiazole-3-thione.

7. The method of claim 1, wherein said 1,2-benzisothiazole derivative is N-iso-propyl 1,2-benzisothiazole-3-thione.

8. The method of claim 1, wherein said 1,2-benzisothiazole derivative is 6-nitro N-acetyl 1,2-benzisothiazolone.

9. The method of claim 1, wherein said 1,2-benzisothiazole derivative is 5-nitro N-n-butyl 1,2-benzisothiazolone.

10. The method of claim 1, wherein said 1,2-benzisothiazole derivative is 5-nitro N-methyl 1,2-benzisothiazolone.

11. The method of claim 1, wherein said 1,2-benzisothiazole derivative is N-ethyl 1,2-benzisothiazole-3-thione.

12. The method of claim 1, wherein said spermicidally effective amount of 1,2-benzisothiazole derivative is from 0.003 grams to 0.010 grams for each vaginal administration.

13. A method in accordance with claim 1, wherein said 1,2-benzisothiazole is in combination with an inert vaginal excipient.

14. The method of claim 13, wherein the amount of the 1,2-benzisothiazole derivative is comprised between 0.1 and 1% by weight based on the composition.

15. The method of claim 13 wherein said spermicidally effective amount of 1,2-benzisothiozole derivative is from 0.003 grams to 0.010 grams for each vaginal administration.

* * * * *